United States Patent
Sage et al.

(10) Patent No.: US 8,777,932 B2
(45) Date of Patent: Jul. 15, 2014

(54) CATHETER CONNECTORS AND SYSTEMS, AND METHODS OF USING SAME

(75) Inventors: Shahn S. Sage, Andover, MN (US); David W. Lodin, Maple Grove, MN (US); Bruce A. Behymer, Grant, MN (US)

(73) Assignee: Medtronic, Inc., Minneapolis, MN (US)

( * ) Notice: Subject to any disclaimer, the term of this patent is extended or adjusted under 35 U.S.C. 154(b) by 964 days.

(21) Appl. No.: 12/770,292

(22) Filed: Apr. 29, 2010

(65) Prior Publication Data
US 2011/0270230 A1 Nov. 3, 2011

(51) Int. Cl.
*A61M 25/16* (2006.01)

(52) U.S. Cl.
USPC .......... 604/535; 604/533; 604/534; 604/536; 604/537; 604/538; 604/539

(58) Field of Classification Search
USPC .......... 604/174, 178, 533–539; 285/243, 255, 285/25, 259
See application file for complete search history.

(56) References Cited

U.S. PATENT DOCUMENTS

| | | | |
|---|---|---|---|
| 1,113,080 A | 10/1914 | Wilson | |
| 3,447,819 A | 6/1969 | Borsum et al. | |
| 3,482,857 A | 12/1969 | Gohs | |
| 4,013,310 A | 3/1977 | Dye | |
| 4,192,532 A | 3/1980 | Pacella | |
| 4,334,551 A | 6/1982 | Pfister | |
| 4,405,163 A | 9/1983 | Voges et al. | |
| 4,526,572 A | 7/1985 | Donnan et al. | |
| 4,592,749 A | 6/1986 | Ebling et al. | |
| 4,610,468 A | 9/1986 | Wood | |
| 4,632,435 A | 12/1986 | Polyak | |
| 4,636,204 A | 1/1987 | Christopherson et al. | |
| 4,691,943 A | 9/1987 | DeLand et al. | |
| 4,704,103 A | 11/1987 | Stöber et al. | |
| 4,834,719 A | 5/1989 | Arenas | |
| 4,890,866 A | 1/1990 | Arp | |
| 4,895,570 A | 1/1990 | Larkin | |
| 4,929,236 A | 5/1990 | Sampson | |
| 4,994,048 A | 2/1991 | Metzger | |
| 5,209,740 A | 5/1993 | Bryant et al. | |
| 5,240,289 A * | 8/1993 | Gottling et al. | 285/24 |
| 5,290,253 A | 3/1994 | Kira | |
| 5,405,339 A * | 4/1995 | Kohnen et al. | 604/535 |
| 5,456,676 A | 10/1995 | Nelson et al. | |
| 5,613,945 A | 3/1997 | Cai et al. | |
| 5,637,102 A | 6/1997 | Tolkoff et al. | |

(Continued)

FOREIGN PATENT DOCUMENTS

EP 1 466 645 A2 10/2004
EP 1 466 645 A3 4/2005

(Continued)

*Primary Examiner* — Bhisma Mehta
*Assistant Examiner* — Larry R Wilson
(74) *Attorney, Agent, or Firm* — Mueting, Raasch & Gebhardt, P.A.

(57) ABSTRACT

Catheter connectors, systems, and methods of use in which a catheter is attached to a connector such that the catheter is retained on the connector by inward radial compression between an outer surface of a hollow pin located within the catheter and a collet fitted over the portion of the catheter containing the pin. The collet may be moved from an unlocked position to a locked position by axial displacement of the collet along a longitudinal axis of the connector.

21 Claims, 8 Drawing Sheets

(56) References Cited

U.S. PATENT DOCUMENTS

| | | |
|---|---|---|
| 5,913,852 A | 6/1999 | Magram |
| 6,402,207 B1 | 6/2002 | Segal et al. |
| 6,456,676 B1 | 9/2002 | O'Connor et al. |
| 6,506,182 B2 | 1/2003 | Estabrook et al. |
| 6,517,115 B1 | 2/2003 | Blivet |
| 6,554,802 B1 | 4/2003 | Pearson et al. |
| 6,641,177 B1 | 11/2003 | Pinciaro |
| 6,796,586 B2 * | 9/2004 | Werth ................... 285/243 |
| 6,817,995 B1 | 11/2004 | Halpern |
| 6,910,906 B2 | 6/2005 | Schorn |
| 6,971,390 B1 | 12/2005 | Vasek et al. |
| 6,997,919 B2 | 2/2006 | Olsen et al. |
| 7,331,613 B2 | 2/2008 | Schulte |
| 7,387,624 B2 | 6/2008 | Nelson |
| 7,537,245 B2 | 5/2009 | Cross, Jr. |
| 7,678,101 B2 | 3/2010 | Sage |
| 2003/0181849 A1 | 9/2003 | Castellanos |
| 2004/0039373 A1 | 2/2004 | Harding et al. |
| 2004/0204690 A1 | 10/2004 | Yashiro et al. |
| 2005/0033371 A1 | 2/2005 | Sommer et al. |
| 2005/0085794 A1 | 4/2005 | Denoth et al. |
| 2005/0107739 A1 | 5/2005 | Palma |
| 2005/0137614 A1 | 6/2005 | Porter et al. |
| 2005/0251102 A1 | 11/2005 | Hegland et al. |
| 2008/0103476 A1 | 5/2008 | Schulte |
| 2008/0275427 A1 | 11/2008 | Sage |
| 2008/0275429 A1 * | 11/2008 | Sage ................... 604/536 |
| 2011/0270231 A1 | 11/2011 | Nelson |

FOREIGN PATENT DOCUMENTS

| | | |
|---|---|---|
| EP | 1 501 583 B1 | 5/2006 |
| EP | 1 466 645 B1 | 8/2007 |
| GB | 2 318 846 A | 5/1998 |
| WO | WO 94/23775 A1 | 10/1994 |
| WO | WO 97/25562 A1 | 7/1997 |
| WO | WO 03/030985 A2 | 4/2003 |
| WO | WO 03/030985 A3 | 7/2003 |

* cited by examiner

CATHETER CONNECTORS AND SYSTEMS, AND METHODS OF USING SAME

TECHNICAL FIELD

The present invention relates generally to medical connection systems and, more particularly, to connectors, systems, and methods for connecting a catheter to another catheter or other device.

BACKGROUND

In many medical applications, it is necessary to connect one section of medical tubing, e.g., a catheter, with another. Generally speaking, it is important that these connections be relatively secure and stable so that the catheter does not separate or develop leaks. Security and leak-resistance take on elevated importance in applications where the catheters are implanted within a human body.

One procedure that necessitates implantation of a catheter into the body involves the use of an implantable medical device, e.g., a drug infusion pump. Such implantable medical devices are often used to control pain and/or spasticity, as well as to provide one or more drugs or fluid medications to a particular location within the body. A typical implant procedure may involve implanting a drug infusion pump into a cavity or subcutaneous pocket in the body and delivering a drug, via one or more catheters, to an epidural space or intrathecal space of the spinal column, or to a particular location within the brain.

An exemplary procedure may include positioning a first catheter at the desired location in the body and then connecting the first catheter to a second catheter via a connector. The connection may be made by inserting one end of the connector into a lumen of one catheter and the other end of the connector into the lumen of the other catheter and then sliding both catheter sections towards one another (toward the middle of the connector). The second catheter may then be connected to the drug infusion pump.

While adequate, difficulties have been encountered in the manufacture and use of such connectors. For example, one or both of the catheters may incorporate a braid in the catheter wall. The braid may provide various benefits including, for example, increased radial, longitudinal, and torsional stiffness. While these attributes are beneficial, the braid may also limit the expansion capacity of the catheter(s). As a result, radial expansion of the inner diameter of the catheters resulting from insertion of the ends of the connector into the catheter may be limited. Also, these connectors, which have been sized to fit within the lumens of the catheters, are small and may be difficult to manipulate by a clinician during implantation. Other potential problems may include lack of ability to adequately secure the catheters relative to the connector; and an inability to provide sufficient strain relief to the catheters at the connector. These issues may result in a weakened connection that is susceptible to catheter separation and/or leaks.

SUMMARY OF THE INVENTION

The present invention provides catheter connectors, connection systems, and methods in which a catheter is attached to a connector such that the catheter is retained on the connector by radial compression between a tube or pin located within the catheter and a collet positioned over the portion of the catheter containing the tube.

In one embodiment, a catheter connection system is provided and includes: a connector pin comprising a first end configured for insertion into a lumen of a catheter, the connector pin including an outer surface; a coupling sleeve configured to surround at least a portion of the catheter that contains the connector pin; and a tubular collet surrounding an end of the sleeve. The collet is movable along a longitudinal axis of the sleeve from an unlocked position to a locked position. The collet includes an outer ring; an inner ring; and an annular space between the inner and outer rings. The inner ring includes one or more segments that deflect inwardly to radially compress the catheter against the outer surface of the pin when the collet is in the locked position. In one configuration, the end of the sleeve is received within the annular space of the collet when the collet is in the locked position. The sleeve may define an inner surface having a tapered surface operable to slide along the one or more segments of the inner ring as the collet is moved from the unlocked position to the locked position. In another configuration, the connector pin is fixed within the sleeve. In yet another configuration, an outer surface of the sleeve comprises radially protruding elements. For instance, the radially protruding elements may be tabs that engage openings formed in the collet to secure the collet in the locked position. Alternatively or additionally, the radially protruding elements may include guide tabs configured to slide within slots in the collet. In still yet another configuration, the one or more segments of the inner ring may include four segments. In another configuration, the collet may define a passageway configured to receive the catheter and align the catheter with the first end of the connector pin. In still another configuration, the connector pin includes a tapered section transitioning the outer surface of the pin from a first diameter at the first end, to a second, larger diameter towards a center of the pin. In yet another configuration, the connector pin includes one or more circumferential barbs located proximate the first end. And in yet another configuration, the pin includes a second end for insertion into a lumen of a second catheter.

In another embodiment, a catheter connection system is provided that includes a connector body having: a tubular coupling sleeve including a wall defined by an inner surface and an outer surface, wherein the inner surface diverges to form an enlarged mouth at an end of the sleeve; and a tubular connector pin fixed relative to the inner surface of the sleeve such that an end of the pin extends outwardly into or beyond the enlarged mouth. The system further includes a catheter defining a lumen configured to receive the end of the connector pin therein. A first end of the catheter is located within the enlarged mouth of the sleeve when the end of the connector pin is received within the lumen of the catheter. A tubular collet is also included and is configured to both: surround a portion of the catheter containing the connector pin; and interlock with the sleeve. The collet is movable along a longitudinal axis of the sleeve from an unlocked position to a locked position. The collet includes an outer ring; an inner ring; and an annular space between the inner and outer rings, wherein the end of the sleeve is received within the annular space when the collet is in the locked position. In one configuration, the mouth defines a tapered surface that diverges towards the end of the sleeve. In another configuration, the tapered surface is configured to slide along the inner ring and deflect the inner ring radially inwardly as the collet is moved to the locked position. In yet another configuration, an outer surface of the pin comprises a tapered section, while in another configuration, an outer surface of the pin includes a circumferential barb. In still another configuration, the connector pin includes a second end extending into an enlarged mouth at a second end of the sleeve, wherein the system further includes: a second catheter defining a lumen configured to receive the second end of the pin; and a second collet associated with the second end of the sleeve.

In yet another embodiment, a therapeutic substance delivery system is provided that includes: an implantable medical device; a delivery catheter for coupling with the medical device; and a catheter connector. The connector includes: a connector pin comprising a terminal end configured for insertion into a lumen of the delivery catheter, the connector pin including an outer surface; a coupling sleeve configured to surround at least a portion of the delivery catheter that contains the connector pin; and a tubular collet surrounding an end of the sleeve. The collet is movable along a longitudinal axis of the sleeve from an unlocked position to a locked position. The collet further includes an outer ring; an inner ring; and an annular space between the inner and outer rings. The inner ring includes one or more segments that deflect inwardly to radially compress the delivery catheter against the outer surface of the pin when the collet is in the locked position. In one configuration, the catheter connector forms part of the medical device. In another configuration, the catheter connector couples the delivery catheter to a therapy catheter.

In still yet another embodiment, a method of connecting a catheter to a tubular connector pin is provided and includes: inserting an end of the connector pin into a lumen of the catheter, the connector pin surrounded by a coupling sleeve radially spaced-apart from the end of the connector pin; and sliding a tubular collet over the sleeve from an unlocked position to a locked position, wherein the collet comprises an outer ring; an inner ring; and an annular space between the inner and outer rings, and wherein the inner ring includes one or more deflectable segments. The method further includes: locating an end of the sleeve in the annular space of the collet; contacting the inner ring of the collet with an inner surface of the sleeve; deflecting the one or more deflectable segments radially inwardly; and compressing the catheter against an outer surface of the pin. In one configuration, the method further includes engaging a tab associated with the sleeve with an opening associated with the collet when the collet reaches the locked position. In another configuration, contacting the inner ring of the collet with the inner surface of the sleeve includes contacting the inner ring with a tapered surface of the inner surface of the sleeve.

The above summary is not intended to describe each embodiment or every implementation of the present invention. Rather, a more complete understanding of the invention will become apparent and appreciated by reference to the following Detailed Description of Exemplary Embodiments in view of the accompanying figures of the drawing.

BRIEF DESCRIPTION OF THE VIEWS OF THE DRAWING

The present invention will be further described with reference to the views of the drawing, wherein:

FIGS. 2A-2B illustrate exemplary implantable applications incorporating various connectors in accordance with embodiments of the present invention, wherein.

The figures are rendered primarily for clarity and, as a result, are not necessarily drawn to scale.

DETAILED DESCRIPTION OF ILLUSTRATIVE EMBODIMENTS

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

As used herein, "a," "an," "the," "at least one," and "one or more" are used interchangeably. The term "and/or" (if used) means one or all of the listed elements or a combination of any two or more of the listed elements. Moreover, where convenient, similar or identical components that are identified with the same reference numeral may be distinguished with the suffix "a" (e.g., 102a). It is understood that a component having such a suffix is, however, similar or identical to the component without the suffix. Further, the description of a component (e.g., catheter 102) provided herein is understood, unless, otherwise stated, to apply to both components (e.g., both to the component without the suffix (102) and to the component with the suffix (102a)).

Illustrative embodiments of the present invention include a tubing connector and system for coupling sections of tubing, and to methods for using the same. In one embodiment, the connector provides a pin that may fit into each tubing section. A coupling sleeve associated with the pin may be located over a portion of the pin and the section(s) of tubing into which the pin extends. One or more tubular collets surrounding one or both ends of the sleeve may then slide, relative to the sleeve, and interlock with the same. The collets, via the sleeve, may radially compress the sections of tubing against the pin, thereby providing a compression force to seal the tubing to the pin and secure the various components in place. In one embodiment, the interlocking of the collets with the coupling sleeve may occur without the use of tools.

Figure 1:
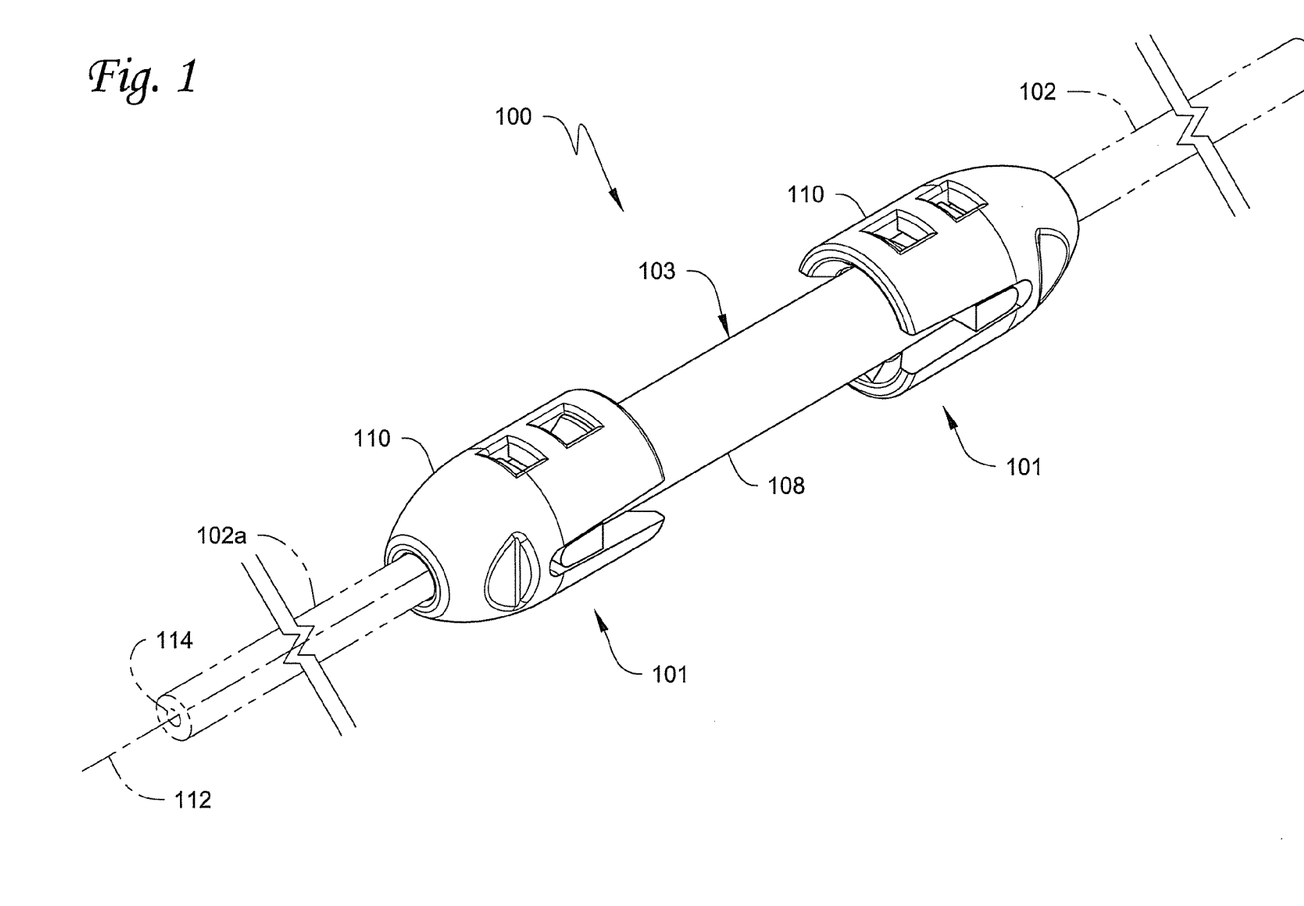
FIG. 1 is a perspective view of a catheter connection system utilizing a connector in accordance with one embodiment of the present invention.

FIG. 1 is a perspective view of a catheter connection system 100 in accordance with one embodiment of the invention. As shown in this figure, the system 100 may include a connector 101 that securely interconnects a first medical tube, e.g., first or delivery catheter 102, with a second medical tube, e.g., second or therapy catheter 102a. The exemplary connector 101 may include a tubular connector pin 106 (see FIG. 3) and associated tubular coupling sleeve 108 (also see FIG. 3), which together form a connector body 103, and two tubular connectors or collets 110. The sleeve 108 is, in one embodiment, configured to surround at least a portion of the catheter (s) that contains the connector pin 106 as further described below. The components 102, 106, 108, and 110 may, when assembled, lie along a longitudinal axis 112 as shown in FIG. 1. Embodiments of the components, connectors, and systems described herein may be sized for implantation within a typical human or other mammalian body.

Figure 2A:
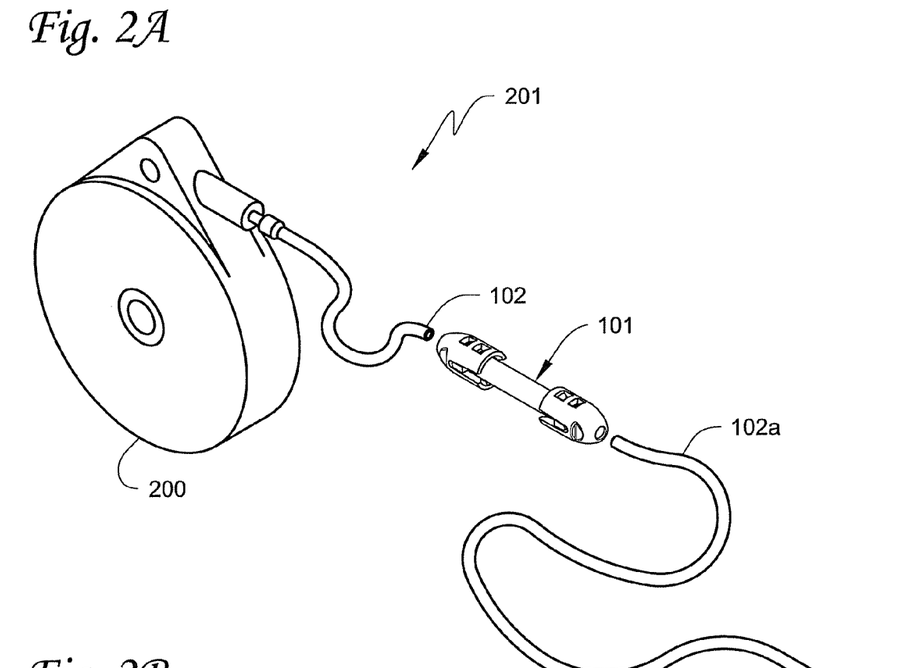
FIG. 2A illustrates an implantable therapeutic delivery system with a two-sided connector.
Figure 2B:
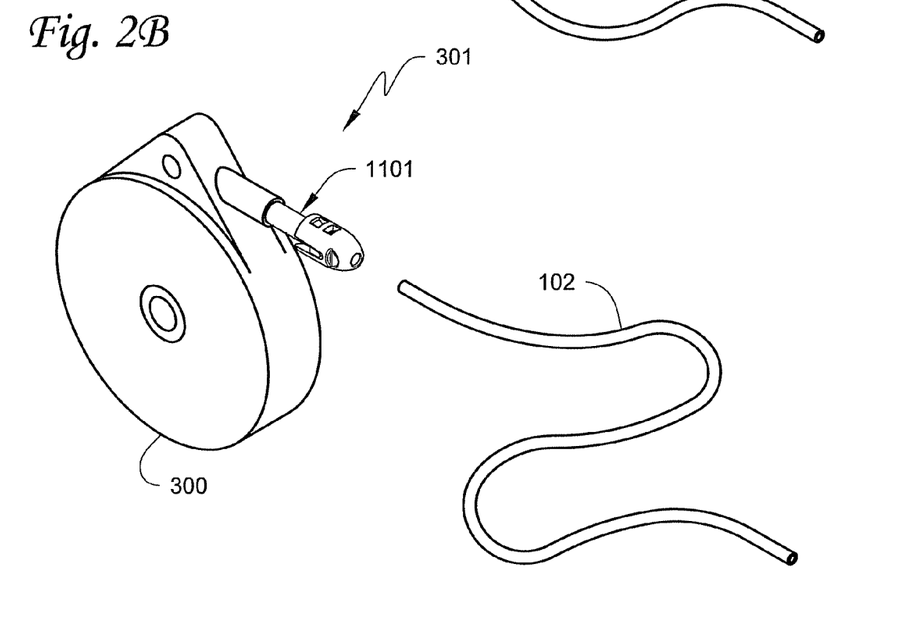
FIG. 2B illustrates a delivery system with a single-sided connector.

Although the system 100 is illustrated as incorporating a two-sided connector, i.e., the illustrated connector 101, includes a collet 110 on each of two opposing ends, other embodiments may utilize a connector having a collet on only one end without departing from the scope of the invention, e.g., a single-sided connector. Exemplary two-sided connectors 101 may be used to, for instance, couple two catheters together, e.g., first and second catheters 102, 102a that couple an implantable medical device (e.g., an implantable infusion pump 200 such as a SynchroMed® II programmable infusion pump distributed by Medtronic, Inc., of Minneapolis, Minn. USA) to a remote drug delivery site, as shown in the therapeutic substance delivery system 201 of FIG. 2A. A single-sided connector 1101 may, on the other hand, be utilized to connect a component (e.g., a pump 300 of a delivery system 301) to a catheter (catheter 102) as shown in FIG. 2B. In case of the latter, the connector 1101, e.g., the body of the connector, may be an integral component of the pump 300 (or otherwise attached thereto).

In yet other embodiments of the present invention, a connector system may again be configured as a two-sided connector, but include different connector structures on each side. For example, one side of the connector may be configured in accordance with an embodiment of the present invention, while the other side of the connector may include an entirely different connector structure.

In still other embodiments, the connector may include more than two sides. For instance, the connector body could form a "Y"-connector including three or more sides, one or more of which may be a connector in accordance with an embodiment of the present invention.

Figure 3:
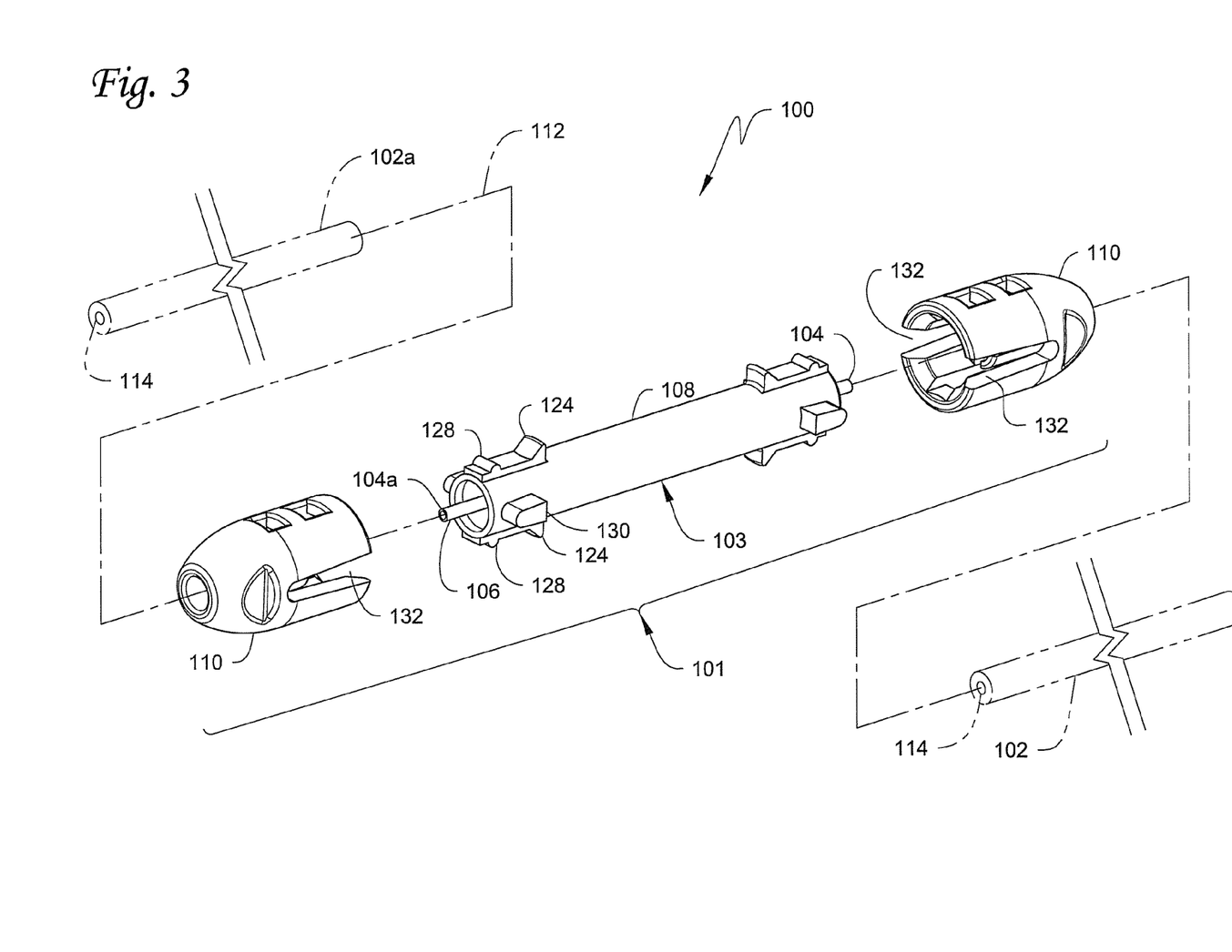
FIG. 3 is an exploded perspective view of the connector and system of FIG. 1.

FIG. 3 illustrates the exemplary connector 101 and connection system 100 of FIG. 1 in an exploded view. While the sleeve 108 (as well as the remaining components of the connection system 100) is shown as having a generally circular cross-sectional shape, any suitable cross-sectional shape could be utilized (e.g., octagonal, elliptical, oval, etc.). However, for reasons that will become clear, regardless of the shape of the sleeve, the engaging portions of the collets 110 will typically include a complementary shape to permit the desired attachment.

As discussed herein, the illustrated system 100 includes a catheter (102, 102a) extending from both sides of the connector (although, once again, single and other multi-sided connectors are contemplated). For brevity, however, the description of the connector 100 may, where appropriate, focus on a single side, with the understanding that the opposite side, if present, is similar or identical.

Each catheter 102 may be of conventional construction, e.g., an elastomeric tubular body made from a polymer (pure or blended), silicone, or the like. The catheter may define a lumen 114 extending end-to-end such that fluids may be delivered through the catheter from one end to the other. One or both catheters may include features, e.g., strengthening braids, multiple layers, additives, etc., to satisfy the particular requirements of the intended application. That is, the construction of the catheters may vary without departing from the scope of the invention. In one embodiment, however, the catheters may be constructed in accordance with, and otherwise similar to, any of the catheter embodiments described and/or illustrated in US Pat. App. Pub. No. US 2008/0275429 A1 (Sage), which is incorporated herein by reference in its entirety.

In the illustrated embodiment, the pin 106 is fixed relative to an inner surface 115 of the sleeve 108, e.g., molded with or otherwise permanently attached to the sleeve, to form the body 103. As evident in the figures (see, e.g., FIG. 4), the pin 106 may be sized where its terminal end(s) 104 extends outwardly into or beyond an enlarged mouth 118 of the sleeve, resulting in the sleeve being radially spaced-apart from the end of the pin. In the illustrated embodiment, the end of the pin 106 may actually protrude a short distance beyond each end of the sleeve 108. However, embodiments wherein the pin is the same length, or even shorter, than the sleeve are certainly possible without departing from the scope of the invention.

As indicated in FIG. 3, each catheter 102, 102a may connect to an end (first end 104 and second end 104a, respectively) of the tubular pin 106 by insertion of the opposing first and second ends of the pin into the respective lumens 114 of the catheters. Stated alternatively, each end of the pin is configured for insertion into the lumen of one of the catheters, and the lumen of each catheter is likewise configured to receive therein an end of the pin. As the pin is hollow (e.g., forms a lumen along its entire length), fluids may thus flow from one catheter through the pin to the other catheter when the connector is fully assembled.

As further shown in FIG. 3, a collet 110 may be associated with at least one end of the sleeve 108 and with at least one of the medical tubes (e.g., one of catheters 102, 102a). In the two-sided connector illustrated in FIG. 3, a collet and a catheter are associated with each end of the sleeve. As described in more detail below, once the catheters are placed over to the ends of the pin 106, the sleeve 108 surrounds the pin 106 and the portions of the catheters 102 that overlap with the pin. Each collet 110 may then be slid towards the center of the sleeve 108 (along the longitudinal axis 112) until it interlocks with the sleeve as further described below. Thus, the collet 110 may both: surround a portion of the catheter containing the pin 106; and interlock with the sleeve 108. Interlocking of the collets 110 with the sleeve 108 may radially compress the catheters 102, 102a against the pin 106, resulting in a strong and leak-free connection.

Figures 4, 5:
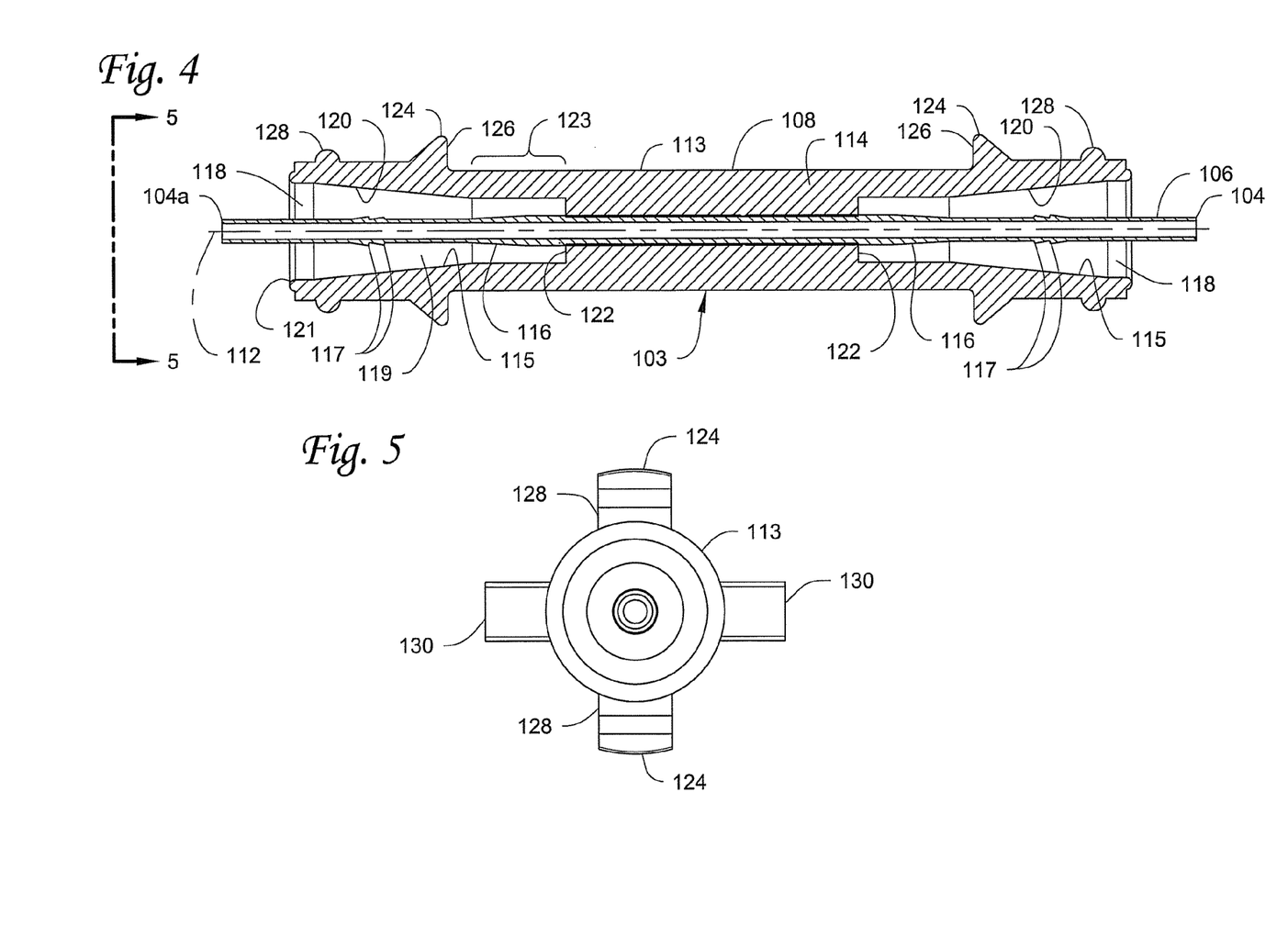
FIG. 4 is cross-sectional view of a body of the connector of FIG. 1.
FIG. 5 is an end view of the body taken along line 5-5 of FIG. 4.

With this brief introduction, an exemplary embodiment of the connector will now be described with reference primarily to FIGS. 4-7. FIG. 4 illustrates a cross sectional view of the body 103 (e.g., sleeve 108 and pin 106) as taken through the longitudinal axis 112, and FIG. 5 illustrates an end view of the body taken along line 5-5 of FIG. 4. As discussed herein above, the pin 106 of the illustrated embodiment is not intended for removal from the sleeve, i.e., the two parts may be permanently attached. In the illustrated embodiment, this attachment may be achieved by molding the pin to the sleeve. However, other methods of attachment, e.g., staking, adhering, press-fits, etc., are certainly possible without departing from the scope of the invention.

The pin 106 may be of a size and material that prevents collapse of the pin under application of radial compression loads applied by the sleeve 108 and collet 110 as further described below. For instance, in one embodiment, the pin is an 80-20 Platinum-Iridium alloy having an inner diameter of about 0.2 millimeters (mm) to about 0.4 mm (e.g., about 0.33 mm) and an outer diameter (measured near each end) of about 0.4 mm to about 0.8 mm (e.g., about 0.48 mm). The pin 106 may further be about 17 mm to about 22 mm (e.g., about 20 mm) long and may include an outer surface having one or more radially protruding, circumferential barbs 117 located proximate each end of the pin as shown in FIG. 4. The pin may additionally include one or more tapered sections 116 spaced inwardly from the each end of the pin (e.g., inboard from the barbs). Each tapered section 116 may transition the outer surface of the pin from a first diameter at the end of the pin, to a second larger diameter towards a center of the pin.

The barbs 117 may assist with retention of the catheters 102 once the ends of the pin 106 are inserted therein. The tapered sections 116, on the other hand, may provide increased interference between the pin and the catheters as the latter are slid over the pin. This increased interference may provide feedback (e.g., resistance to sliding) to the clinician as to when the pin 106 has been adequately inserted into its respective catheter. The tapered sections 116 may further provide a transition to a larger diameter towards the center of the pin that is beneficial to the manufacture of the body 103. Once again, while the pin 106 is described with some particularity herein, such a construction is intended to be exemplary only as other materials (e.g., titanium), sizes, and configurations are certainly contemplated.

As illustrated in FIG. 4, the sleeve 108 may also form a tubular member having a wall 114 defined by an outer surface 113 and the inner surface 115. While again not wishing to be bound to any particular configuration, the sleeve 108 may, in one embodiment have an outer diameter (measured near its center) of about 2 mm to about 5 mm (e.g., about 2.5 mm). The sleeve may further have a length (measured along the longitudinal axis 112) of about 15 mm to about 20 mm (e.g., about 17.5 mm). With the pin 106 secured within the sleeve 108 as shown in FIG. 4, the sleeve may surround portions of the pin and, when assembled with the catheters 102, portions of the catheters that overlap with the pin (see, e.g., FIG. 9). In one embodiment, the pin 106 may protrude longitudinally about 1 mm to about 5 mm beyond each end of the sleeve 108.

The inner surface 115 may have a profile that varies along a length of the sleeve 108. For instance, at one or both ends of the sleeve 108, the inner surface 115 may transition or expand to form the enlarged mouth 118. This transition may be accommodated in a variety of ways. For instance, in one embodiment, the inner surface 115 may include a tapered portion or surface 120 that tapers from the mouth 118 inwardly towards a center portion of the sleeve (e.g., diverges towards the end of the sleeve). The inner surface 115, e.g., the mouth 118, may optionally include a transition area 123 extending inwardly from the tapered surface 120 to a step surface 122 that is, in one embodiment, perpendicular to the longitudinal axis 112 of the sleeve. In one embodiment, the transition area of the sleeve 108 is defined by a generally uniform diameter as shown in FIG. 4 that is of a diameter sufficient to receive the catheter and permit it some degree of axial movement during catheter connection.

The sleeve 108 may further include features that permit and assist with mechanical coupling of the sleeve with the collets 110. For instance, in one embodiment, the outer surface 113 may form one or more radially protruding elements, e.g., tabs 124, which extend away from the longitudinal axis 112 as shown in FIGS. 4 and 5. The outer surface 113 of the sleeve 108 may optionally define one or more secondary tabs 128. As described below, the tabs 124 may each foam a surface 126 that, along with the secondary tab 128, interact with corresponding features of the collet 110. In the illustrated embodiment, the secondary tabs 128 allow the collet 110 to be pre-mounted onto the sleeve 108. Pre-mounting the collet to the sleeve may not only reduce the presence of otherwise loose and separate parts, it also provides an alignment feature to assist with placing the catheter over the pin.

As shown in FIG. 5, each end of the body 103 may include both a tab 124 and a tab 128 at two separate locations that are spaced 180 degrees from one another. Other embodiments may include more or less tabs without departing from the scope of the invention.

In the illustrated embodiment, other radially protruding elements, e.g., guide tabs 130, may also be included. For instance, each end of the sleeve may include two guide tabs 130 evenly spaced from the tabs 124 (e.g., spaced 90 degrees to each side of the tabs 124). The guide tabs 130, as explained below, may fit and slide within slots 132 (see FIG. 3) formed in the collets 110 to index the collets relative to the connector body 103, thereby preventing incorrect assembly.

Figure 6:
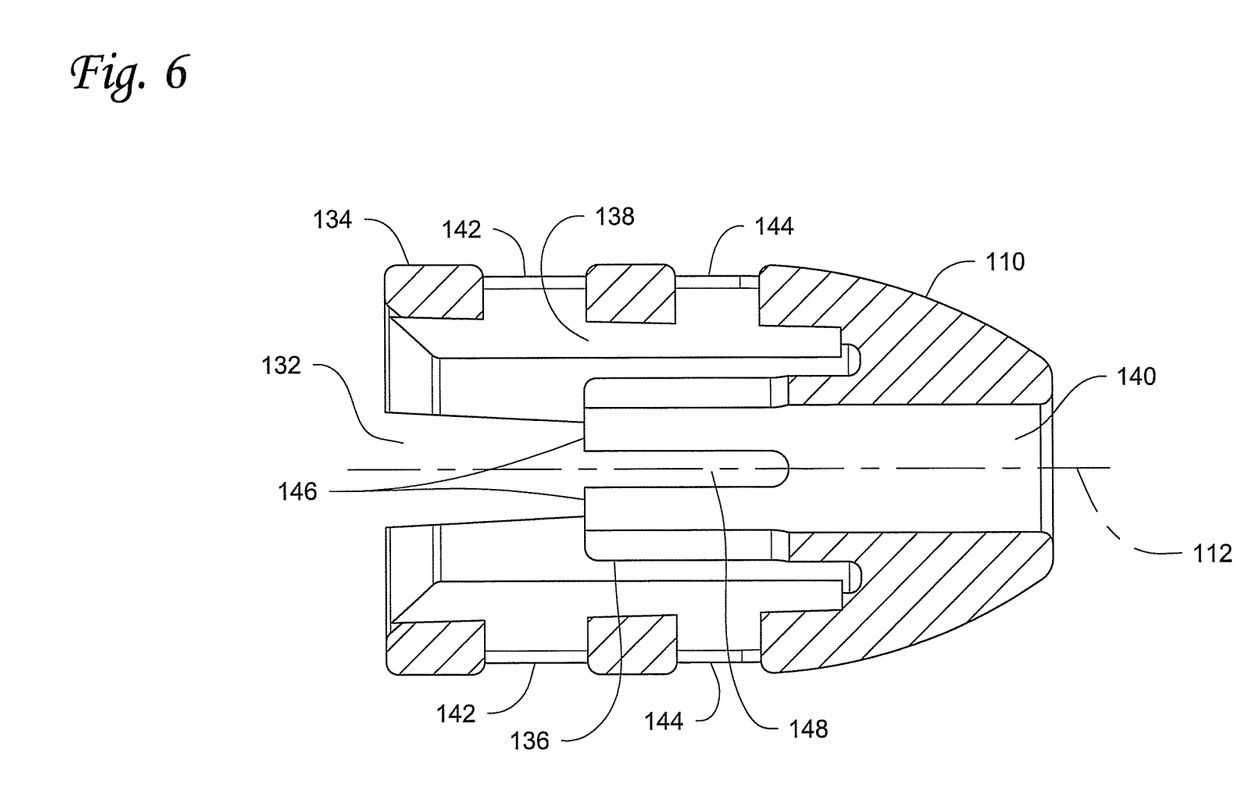
FIG. 6 is cross-sectional view of a locking collet of the connector of FIG. 1.
Figure 7:
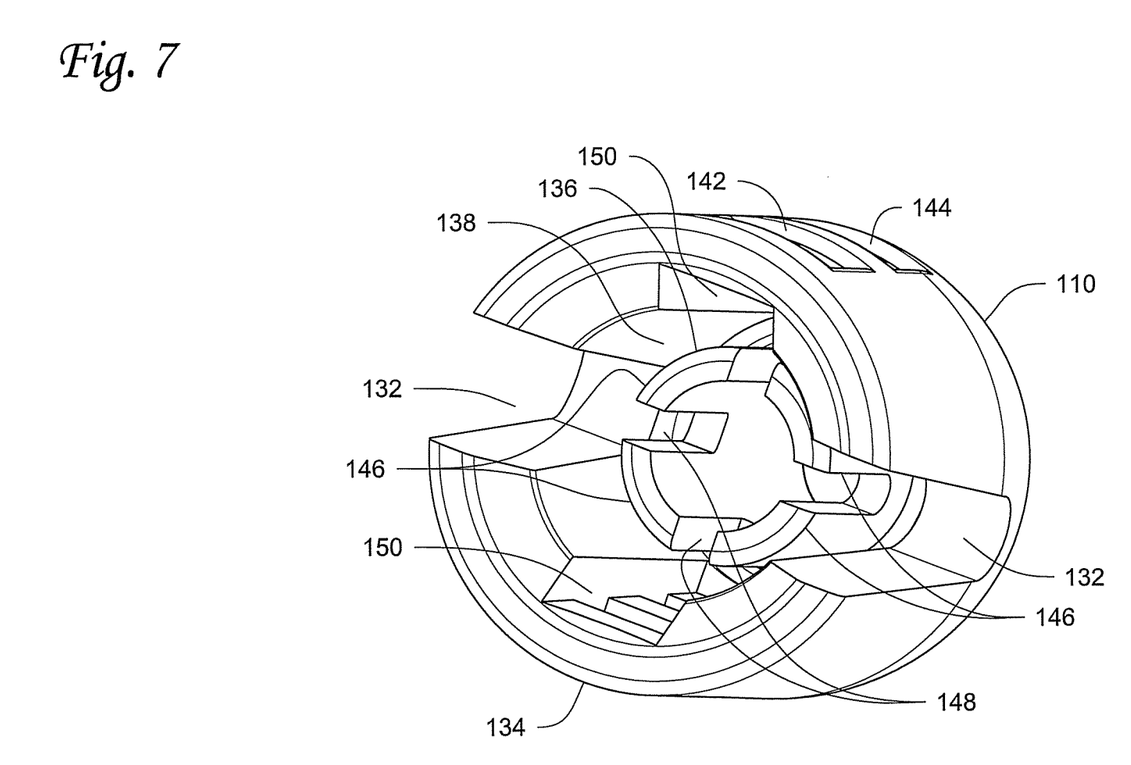
FIG. 7 is a perspective view illustrating an interior of the collet of FIG. 6.

FIGS. 6 and 7 illustrate, respectively, a cross-sectional view and a perspective view of the exemplary collet 110. The collet 110 may, in one embodiment, form a tubular cup-shaped member that is formed by an outer ring 134 and an inner ring 136. Between the inner and outer rings an annular space 138 may be formed. A passageway 140 extends completely through the collet 110 (e.g., through the inner ring 136) along the longitudinal axis 112 to accommodate the catheter 102 and pin 106 as further described herein.

With reference to FIG. 6, the outer ring 134 may also define a series of openings, e.g., first and second openings 142 and 144. These openings may interact with the tabs 124 and 128 as further described below. The outer ring 134 may further define the slots 132 as already described above. The slots may visually divide the outer ring into two halves (see, e.g., FIG. 3).

The inner ring 136 may be partitioned into multiple semi-cylindrical segments or members 146 by slots 148. In the illustrated embodiment, the inner ring 136 has four slots 148 that partition the ring into four cantilevered segments 146 (see FIG. 7). Those of skill in the art, however, will realize that more or less segments 146 may be formed without departing from the scope of the invention.

As shown in FIG. 7, an inner side of the outer ring 134 may also include slots 150 aligned with the openings 142 and 144. These slots 150 may accommodate the protruding structure supporting the tabs 124 and 128 (see FIG. 3) to permit sliding engagement of the collet 110 over the sleeve 108.

While not wishing to be bound to any particular material, both the sleeve 108 and collets 110 may, in one embodiment, be made from nylon 12 (sold under the trade name Grilamid TR55 by EMS-Grivory of Switzerland).

Figure 8:
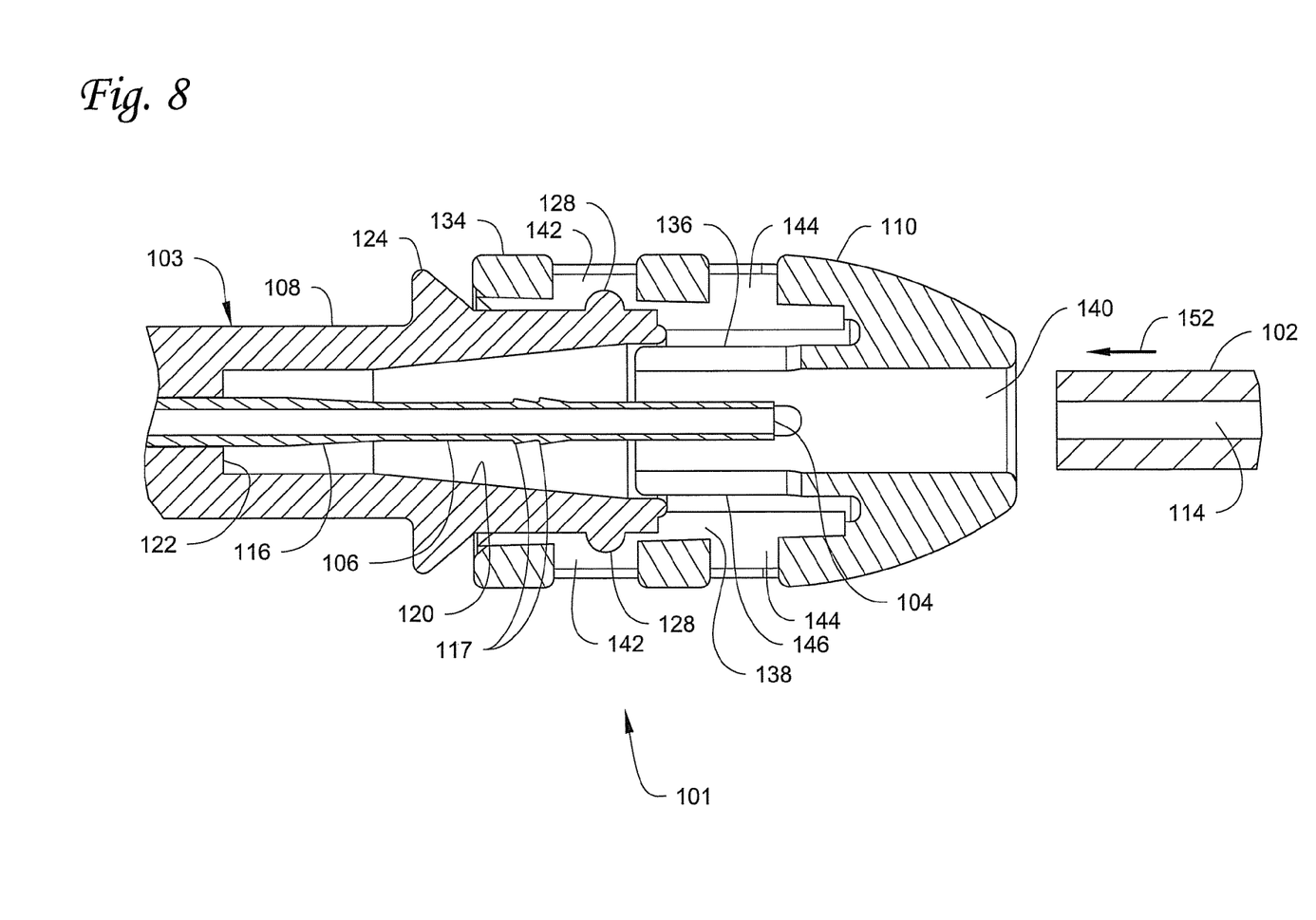
FIG. 8 is an enlarged partial cross-sectional view of the system of FIG. 1 illustrating a method for attaching a catheter to a first end of the connector, wherein the collet of the connector is shown in an unlocked position.
Figure 9:
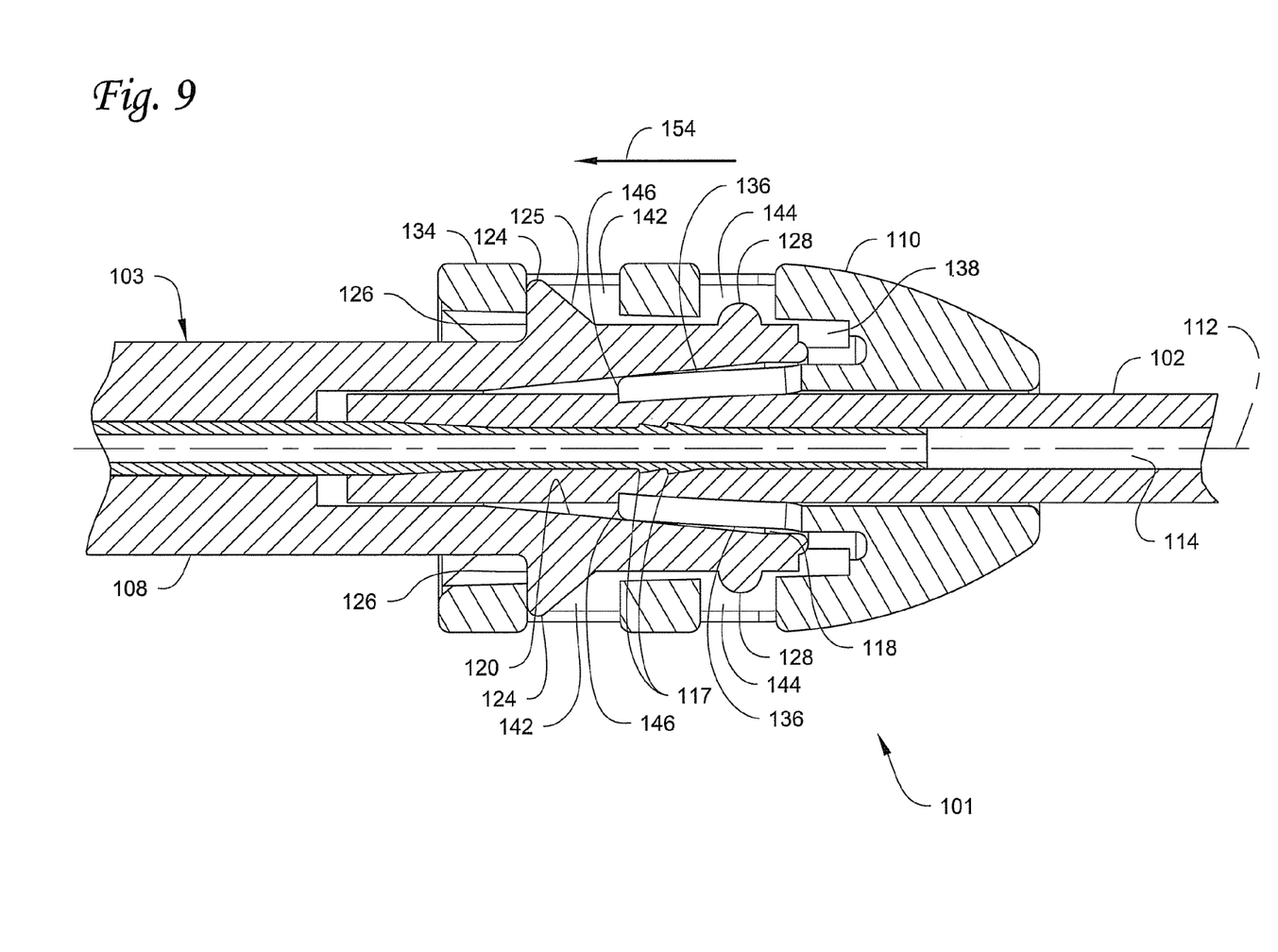
FIG. 9 illustrates the system of FIG. 8 once the catheter is attached and the collet is moved from the unlocked position to a locked position.

A method of using the exemplary connector 101 will now be described primarily with reference to FIGS. 3, 8, and 9. The connector 101 may be supplied with the collet(s) 110 attached to the body 103 and positioned in an unlocked position as shown in FIG. 8. In this manner, the body 103 and collet(s) 110 may be assembled and enclosed in a single sterile package. As further described herein, each collet 110 may be movable, e.g., slidable, along the longitudinal axis 112 of the sleeve 108 from the unlocked position of FIG. 8 to a locked position as shown in FIG. 9 and as described in more detail below.

In the unlocked position, the collet 110 may be positioned on the sleeve 108 such that the secondary tab 128 is aligned with the opening 142 formed in the collet. The engagement of the secondary tab 128 with the opening 142 is sufficient to hold the collet 110 in the unlocked position until the clinician positively advances the collet to the locked position as further explained below. The tab 124 may also assist in holding the collet 110 in the unlocked position by contact with the edge of the collet as shown in FIG. 8.

To couple the catheter 102 to the connector 101, the catheter 102 may be received into the passageway 140 formed in the collet 110 as represented by the direction arrow 152 in FIG. 8. The diameter of the passageway 140 may be sized to assist with aligning the catheter 102 (e.g., the lumen 114 of the catheter) with the end 104 of the pin 106 so that the pin may be more easily inserted into the lumen of the catheter.

As the catheter 102 is slid sufficiently onto the pin 106, it eventually passes over the barbs 117 and ultimately, engages the tapered section 116. The tapered section 116 may provide further resistance to catheter advancement, providing the clinician with feedback that the catheter 102 has been adequately received over the pin 106. If the catheter is advanced further, it may eventually abut the step surface 122. When the pin 106 is adequately received within the lumen 114 of the catheter 102, the catheter is located within the enlarged mouth 118 of the sleeve as shown in FIG. 9.

With the catheter 102 attached to the pin 106, the collet 110 may then be advanced, e.g., slid, towards the center of the body 103, e.g., in the direction 154 indicated in FIG. 9. As the collet is advanced from the unlocked position of FIG. 8 to the locked position of FIG. 9, the outer ring 134 of the collet may ride over the tab 124 until the tab 124 engages the opening 142. Each tab 124 may include a ramped surface 125 (see FIG. 9) to assist with advancement of the collet. Once the collet is advanced to the locked position shown in FIG. 9, the tab 124 associated with the sleeve is aligned and engaged with the opening 142 of the collet and the tab 128 is aligned and engaged with the opening 144. At this point, the surface 126 of the tab 124 is in abutment with an inner surface of the opening 142. The surface 126 may be generally perpendicular to the longitudinal axis to provide positive latching (e.g., a ratcheting or snap-fit connection) of the collet to the body 103. Such positive latching may be indicated, for example, by tactile, audible, or visual cues. The surface 126 is also constructed so that retraction of the collet (e.g., return of the collet to the unlocked position of FIG. 8) is difficult or nearly impossible (short of damaging or destroying one or more components).

As the collet 110 advances from the unlocked position to the locked position, the inner ring 136 of the collet enters the mouth 118 of the sleeve 108 and the end of the sleeve is received within the annular space 138 (see FIGS. 6 and 8) formed between the inner ring and the outer ring 134 of the collet. As a result, the tapered surface 120 slides along the inner ring, e.g., along the segments 146 (FIG. 6) that form the inner ring. The tapered surface 120 causes the segments 146 of the inner ring to deflect inwardly to radially compress the catheter 102 against the outer surface of the, pin 106 (as the collet is moved towards the locked position as illustrated in FIG. 9). In one embodiment, the compressive force applied by the segments 146 is at least partially distributed over a portion of the catheter that is at or near (and, in one embodiment, slightly inboard of) the barbs 117. Accordingly, the catheter is securely attached to the pin by a radial compressive force applied by the sleeve 108 of the body 103 to the segments 146.

In one embodiment, the method may also include tunneling subcutaneously a proximal end of the catheter 102 (see, e.g., FIG. 2B), which has its opposite or distal therapy-delivering end implanted at the desired anatomical location, to the area where the implantable pump 300 is positioned. This proximal end may then be coupled to the connector 1101 of the pump in accordance with methods described above. In yet another embodiment (e.g., where the connector is configured as a two-sided connector 101 as shown in FIG. 2A), the method may include positioning the therapy-delivering end of the catheter 102a in a similar manner such that its proximal end may couple to a first side of the connector 101. In this embodiment, the method may also include coupling a distal end of the catheter 102 to a port of the implanted pump 200 and its opposite or proximal end to a second side of the connector 101 as described herein.

To remove the connector 101, the catheter(s) 102 may be cut and the connector disposed of. Alternatively, a medical instrument, e.g., forceps, may be used to push the tab 128 radially inwardly and/or the collet may be deformed sufficiently to permit the collet to return to the unlocked position. At this point, the catheters may be retracted from the pin 106 or cut and removed.

As illustrated in FIG. 9, the collet 110, when in the locked position, may extend beyond the length of the pin 106. As a result, the catheter 102 is provided with some degree of strain relief to reduce potential damage to the catheter from the end of the pin.

Illustrative embodiments of this invention are discussed and reference has been made to possible variations within the scope of this invention. These and other variations, modifications, and combinations of the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A catheter connection system comprising:
   a connector pin comprising a first end configured for insertion into a lumen of a catheter, the connector pin comprising an outer surface;
   a coupling sleeve configured to surround at least a portion of the catheter that contains the connector pin, wherein an outer surface of the sleeve comprises radially protruding elements; and
   a tubular collet surrounding an end of the sleeve, the collet movable along a longitudinal axis of the sleeve from an unlocked position to a locked position, wherein the collet comprises an outer ring; an inner ring; and an annular space between the inner and outer rings, and wherein the inner ring comprises one or more segments that deflect inwardly to radially compress the catheter against the outer surface of the pin when the collet is in the locked position.

2. The system of claim 1, wherein the end of the sleeve is received within the annular space of the collet when the collet is in the locked position.

3. The system of claim 2, wherein the sleeve defines an inner surface comprising a tapered surface operable to slide along the one or more segments of the inner ring as the collet is moved from the unlocked position to the locked position.

4. The system of claim 1, wherein the connector pin is fixed within the sleeve.

5. The system of claim 1, wherein the radially protruding elements comprise tabs that engage openings formed in the collet to secure the collet in the locked position.

6. The system of claim 1, wherein the radially protruding elements comprise guide tabs configured to slide within slots in the collet.

7. The system of claim 1, wherein the one or more segments of the inner ring comprises four segments.

8. The system of claim 1, wherein the collet defines a passageway configured to receive the catheter and align the catheter with the first end of the connector pin.

9. The system of claim 1, wherein the connector pin comprises a tapered section transitioning the outer surface of the pin from a first diameter at the first end, to a second, larger diameter towards a center of the pin.

10. The system of claim 1, wherein the connector pin comprises one or more circumferential barbs located proximate the first end.

11. The system of claim 1, wherein the pin comprises a second end for insertion into a lumen of a second catheter.

12. A catheter connection system comprising:
a connector body comprising:
   a tubular coupling sleeve comprising a wall defined by an inner surface and an outer surface, wherein the inner surface diverges to form an enlarged mouth at an end of the sleeve, wherein the inner surface of the mouth further defines a tapered surface that diverges towards the end of the sleeve; and
   a tubular connector pin fixed relative to the inner surface of the sleeve such that an end of the pin extends outwardly into or beyond the enlarged mouth;
a catheter defining a lumen configured to receive the end of the connector pin therein, wherein a first end of the catheter is located within the enlarged mouth of the sleeve when the end of the connector pin is received within the lumen of the catheter; and
a tubular collet configured to both: surround a portion of the catheter containing the connector pin; and interlock with the sleeve, the collet movable along a longitudinal axis of the sleeve from an unlocked position to a locked position, wherein the collet comprises an outer ring; an inner ring; and an annular space between the inner and outer rings, and wherein the end of the sleeve is received within the annular space when the collet is in the locked position.

13. The system of claim 12, wherein the tapered surface is configured to slide along the inner ring and deflect the inner ring radially inwardly as the collet is moved to the locked position.

14. The system of claim 12, wherein an outer surface of the pin comprises a tapered section.

15. The system of claim 12, wherein an outer surface of the pin comprises a circumferential barb.

16. The system of claim 12, wherein the connector pin comprises a second end extending into an enlarged mouth at a second end of the sleeve, and wherein the system further comprises:
   a second catheter defining a lumen configured to receive the second end of the pin; and
   a second collet associated with the second end of the sleeve.

17. A therapeutic substance delivery system comprising:
an implantable medical device;
a delivery catheter for coupling with the medical device; and
a catheter connector comprising:
   a connector pin comprising a terminal end configured for insertion into a lumen of the delivery catheter, the connector pin comprising an outer surface;
   a coupling sleeve configured to surround at least a portion of the delivery catheter that contains the connector pin, wherein an outer surface of the sleeve comprises radially protruding elements; and
   a tubular collet surrounding an end of the sleeve, the collet movable along a longitudinal axis of the sleeve from an unlocked position to a locked position, wherein the collet comprises an outer ring; an inner ring; and an annular space between the inner and outer rings, and wherein the inner ring comprises one or more segments that deflect inwardly to radially compress the delivery catheter against the outer surface of the pin when the collet is in the locked position.

18. The system of claim 17, wherein the catheter connector forms part of the medical device.

19. The system of claim 17, wherein the catheter connector couples the delivery catheter to a therapy catheter.

20. A method of connecting a catheter to a tubular connector pin, the method comprising:
inserting an end of the connector pin into a lumen of the catheter, the connector pin surrounded by a coupling sleeve radially spaced-apart from the end of the connector pin;
sliding a tubular collet over the sleeve from an unlocked position to a locked position, wherein the collet comprises an outer ring; an inner ring; and an annular space between the inner and outer rings, and wherein the inner ring comprises one or more deflectable segments;
locating an end of the sleeve in the annular space of the collet;
contacting the inner ring of the collet with an inner surface of the sleeve;
deflecting the one or more deflectable segments radially inwardly;
compressing the catheter against an outer surface of the pin; and
engaging a tab associated with an outer surface of the sleeve with an opening associated with the collet when the collet reaches the locked position.

21. The method of claim 20, wherein contacting the inner ring of the collet with the inner surface of the sleeve comprises contacting the inner ring with a tapered surface of the inner surface of the sleeve.

* * * * *